US010353108B2

(12) United States Patent
Huang et al.

(10) Patent No.: US 10,353,108 B2
(45) Date of Patent: Jul. 16, 2019

(54) SECURITY INSPECTION PASSAGE AND SECURITY INSPECTION APPARATUS

(71) Applicant: NUCTECH COMPANY LIMITED, Beijing (CN)

(72) Inventors: Qingping Huang, Beijing (CN); Jia Xu, Beijing (CN); Mingzhi Hong, Beijing (CN); Yanxia Zheng, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 226 days.

(21) Appl. No.: 15/272,175

(22) Filed: Sep. 21, 2016

(65) Prior Publication Data

US 2017/0082777 A1     Mar. 23, 2017

(30) Foreign Application Priority Data

Sep. 22, 2015   (CN) .......................... 2015 1 0608267

(51) Int. Cl.
*G01N 23/04* (2018.01)
*G01V 5/00* (2006.01)
*G01N 23/083* (2018.01)

(52) U.S. Cl.
CPC ......... *G01V 5/0016* (2013.01); *G01N 23/083* (2013.01)

(58) Field of Classification Search
CPC ...... G01V 5/00; G01V 5/0016; G01V 5/0008; G01N 23/00; G01N 23/04; G01N 23/083
USPC .......................................................... 378/57
See application file for complete search history.

(56) References Cited

U.S. PATENT DOCUMENTS

| 5,124,554 | A | 6/1992 | Fowler et al. |
| 5,153,439 | A | 10/1992 | Gozani et al. |
| 8,223,919 | B2 * | 7/2012 | Morton ................ G01N 23/046 378/57 |
| 8,678,169 | B2 | 3/2014 | Baker et al. |
| 9,188,696 | B2 * | 11/2015 | Schafer ................ G01V 5/0016 |
| 2009/0010373 | A1 | 1/2009 | Jestice |
| 2009/0038998 | A1 | 2/2009 | Henkel et al. |

(Continued)

FOREIGN PATENT DOCUMENTS

| CN | 201421439 Y | 3/2010 |
| CN | 101740155 A | 6/2010 |

(Continued)

OTHER PUBLICATIONS

Extended European Search Report as issued in European Patent Application No. 16190244.0, dated Feb. 8, 2017.

(Continued)

*Primary Examiner* — Jurie Yun
(74) *Attorney, Agent, or Firm* — Pillsbury Winthrop Shaw Pittman LLP

(57) ABSTRACT

A security inspection passage and a security inspection apparatus. The security inspection passage includes: an inspection passage main portion that extends along a first direction and through which an item to be inspected passes so as to receive an inspection; an inspection passage entrance end portion configured to be oriented in a direction that is angled at a first angle relative to the first direction; and an inspection passage exit end portion configured to be oriented in a direction that is angled at a second angle relative to the first direction, wherein the first angle and/or the second angle are/is not zero.

20 Claims, 2 Drawing Sheets

(56) References Cited

U.S. PATENT DOCUMENTS

2012/0228377 A1   9/2012   Carpenter et al.
2013/0126303 A1   5/2013   Crass et al.
2015/0212014 A1   7/2015   Sossong et al.

FOREIGN PATENT DOCUMENTS

| CN | 102497942 A | 6/2012 |
| CN | 102511457 A | 6/2012 |
| CN | 103063685 A | 4/2013 |
| CN | 103064126 A | 4/2013 |
| CN | 203037594 U | 7/2013 |
| CN | 203133293 U | 8/2013 |
| CN | 204479765 U | 7/2015 |
| CN | 105116463 A | 12/2015 |
| CN | 205049759 U | 2/2016 |
| WO | WO 2006090181 A2 | 8/2006 |
| WO | WO 2006090181 A3 | 8/2006 |
| WO | WO 2014/022529 A1 | 2/2014 |

OTHER PUBLICATIONS

Office Action as issued in Chinse Patent Application No. 201510608267.3, dated Mar. 3, 2017.
Examination Report as issued in Australian Patent Application No. 2016327243, dated Feb. 9, 2018.
International Search Report as issued in International Patent Application No. PCT/CN2016/090986, dated Oct. 21, 2016.
Written Opinion of the International Searching Authority as issued in International Patent Application No. PCT/CN2016/090986, dated Oct. 21, 2016.
Office Action as issued in Canadian Patent Application No. 2,981,079, dated Jul. 10, 2018.

\* cited by examiner

SECURITY INSPECTION PASSAGE AND SECURITY INSPECTION APPARATUS

TECHNICAL FIELD

Embodiments of the present invention relate to the field of security inspection, and particularly to a security inspection passage and a security inspection apparatus.

BACKGROUND

A conventional security inspection apparatus generally uses an X-ray source to emit X-ray radiation through an item to be inspected, so as to observe whether or not the item carries a suspected article. The item to be inspected is inspected by passing it through an inspection passage. However, a conventional inspection passage is designed such that the X-ray radiation may leak out from entrance and exit of the inspection passage and thus a person who takes his or her item near the entrance and exit will be irradiated by the X-ray radiation. As the X-ray radiation can seriously harm a human body, in order to avoid X-ray radiation leaking out from the inspection passage so as to harm a human body, a shielding structure is provided at, for example, the entrance and exit of the conventional inspection passage to block the X-ray radiation.

SUMMARY

However, when the items to be inspected continuously enter and exit the inspection passage, X-ray radiation will continuously leak out and unavoidably harm a human body near the passage. Thus, it is required to prevent the X-ray radiation from leaking out from the inspection passage to harm a human body.

FIG. 3 illustrates a schematic view of a conventional inspection passage. A main portion 1 in the Figure is a security inspection apparatus, and X-ray radiation may leak out from both ends (as shown by arrows) of the main portion of the inspection passage. A baggage enters the inspection passage 1 from an entrance 11 end of the inspection passage and exits from an exit end 12 of the inspection passage (as shown in FIG. 3, from right to left). A suspected baggage passage 14 and a secured baggage passage 13 are disposed in parallel at the exit end 12 of the inspection passage, and a secured baggage enters, in a straight line, the secured baggage passage 13 from the exit end 12 of the inspection passage and a suspected baggage is turned to the suspected baggage passage 14. Then, the suspected baggage is transferred to a re-inspection baggage back-delivering passage portion 15 that runs in an opposite direction (as shown in FIG. 3, from left to right), and is transferred to a beginning end 10 of the inspection passage. However, the inspection passage occupies a relatively large space and has a relatively massive structure.

Embodiments of the present invention provide a security inspection passage which is able to avoid or eliminate leakage of radiation from harming a human body.

According to an aspect, there is provided a security inspection passage which is able to be used together with a radiation-type security inspection apparatus for security inspection, and the security inspection passage comprises: an inspection passage main portion that extends along a first direction and through which an item to be inspected passes so as to receive an inspection; an inspection passage entrance end portion configured to be oriented in a direction that is angled at a first angle relative to the first direction; and an inspection passage exit end portion configured to be oriented in a direction that is angled at a second angle relative to the first direction, wherein the first angle and/or the second angle are/is not zero.

According to an aspect, there is provided a security inspection apparatus comprising: a radiation source configured to emit radiation beams; a detection device configured to detect radiation beams that are transmitted through an item to be inspected; and the security inspection passage as described above.

DETAILED DESCRIPTION

Description of embodiments of the present invention is provided in detail below and examples are illustrated in Figures, in which the like reference number always represents the like component. For interpretation, the embodiments will be described with reference to the drawings.

According to an embodiment, there is provided a security inspection passage which is able to be used together with a security inspection apparatus that uses radiation. The security inspection passage comprises: an inspection passage main portion 111 that extends along a first direction and through which an item to be inspected passes so as to receive an inspection; an inspection passage entrance end portion 112 (shown as a portion within a dashed line block at the right of FIG. 1, and however it is not limited exactly to be this portion) configured to be oriented in a direction that is angled at a first angle relative to the first direction; and an inspection passage exit end portion 113 (shown as a portion within a dashed line block at the left of FIG. 1, and however it is not limited exactly to be this portion) configured to be oriented in a direction that is angled at a second angle relative to the first direction. For example, in an embodiment, the inspection passage main portion is equipped with a security inspection apparatus such as an X-ray baggage or item security inspection apparatus, a CT baggage or item security inspection apparatus, or the like.

Figure 1:
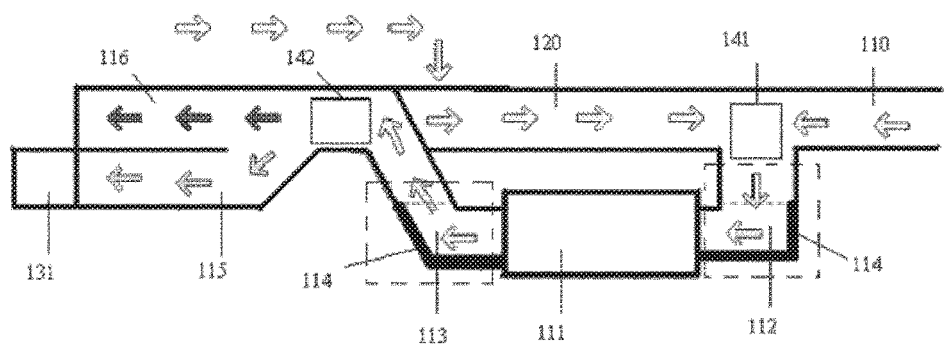
FIG. 1 illustrates a plan view of an upper level of a security inspection passage according to an embodiment.

In the embodiment, as shown in FIG. 1, the first direction is a direction from right to left on the page of FIG. 1. It is noted that the first direction may also be any orientation in the page plane of FIG. 1. It is appreciated that, the direction along which the inspection passage main portion 111 extends may be in any other orientation, and the inspection passage main portion 111 may extend substantially along a linear direction, however, it may be along a curved one or may be along a non-linear one. The inspection passage entrance end portion 112 extends in a direction that deviates by an angle from the direction along which the inspection passage main portion 111 extends. That is, the inspection passage entrance end portion 112 extends along a direction different from that of the inspection passage main portion 111. With this configuration, radiation such as X-ray radiation generated within the inspection passage main portion 111 cannot directly propagate out of the inspection passage main portion 111 from the inspection passage entrance end portion 112, thereby avoiding a person near the inspection passage entrance end portion 112 from being harmed by the radiation. In similar manner, the inspection passage exit end portion 113 extends in a direction that deviates by an angle from the direction along which the inspection passage main portion 111 extends, that is, the inspection passage exit end portion 113 extends along a direction different from that of the inspection passage main portion 111. With this configuration, radiation, such as X-ray radiation, generated within the inspection passage main portion 111 cannot directly propagate out of the inspection passage main portion 111 from the inspection passage exit end portion 113, thereby avoiding a person near the inspection passage exit end portion 113 from being harmed by the radiation.

In an embodiment, the inspection passage main portion 111 includes a radiation shielding device 114 configured to prevent the radiation within the inspection passage main portion 111 from propagating out of the inspection passage main portion 111, and the radiation shielding device 114 extends from the inspection passage entrance end portion 112 to the inspection passage exit end portion 113.

In an embodiment, the security inspection passage further includes an item flow diversion station 142, with which the inspection passage exit end portion 113 is connected. At the item flow diversion station 142, the items which have been inspected are divided into two parts, one are items that are secured or non-suspected and are diverted to a secured item passage portion for secure items, and the other are items that are suspected or items which need to be re-inspected and are diverted to a suspected item passage portion for suspected items.

In an embodiment, the security inspection passage further includes a suspected item passage portion 116 and a secured item passage portion 115. The item flow diversion station 142 is provided with a recognition system, which is connected with a main computer configured for inspection and configured to perform recognition of the item at the item flow diversion station 142 when an item passes through the inspection passage main portion 111. Specifically, when the item passes the inspection passage main portion 111 and is shown to carry a suspected article, the item will be recognized by the recognition system at the item flow diversion station 142 and is diverted to the suspected item passage portion 116 of the security inspection passage. A non-suspected item or secured item is diverted to the secure item passage portion 115.

In an embodiment, the security inspection passage further includes a re-inspected item passage 120 configured to deliver an item to be re-inspected back to the inspection passage entrance end portion 112. For the suspected item in the suspected item passage portion 116, a re-inspection is performed to determine whether it carries a suspected article(s) or not. In an embodiment, there is provided an item re-inspection passage portion 120, and the suspected item is transferred from the suspected item passage portion 116 to the item re-inspection passage portion 120, and then is delivered back to near the inspection passage entrance end portion 112.

In an embodiment, the item flow diversion station 142 is located near a beginning point of the item re-inspection passage portion 120 such that the suspected item can be diverted from the item flow diversion station 142 to the item re-inspection passage portion 120. In an embodiment, there is provided a suspected item transferring passage to transfer the suspected item from suspected item passage portion 116 to the item re-inspection passage portion 120 such that the suspected item may be delivered to near the inspection passage entrance end portion 112 for re-inspection.

In an embodiment, the item re-inspection passage portion 120 extends in a second direction that is opposite to the first direction, and delivers the item therein in a direction opposite to the direction in which the inspection passage main portion 111 delivers the item. In the embodiment, as shown in FIG. 1, the item re-inspection passage portion 120 extends from left to right in the page of FIG. 1. In an embodiment, the item re-inspection passage portion 120 extends linearly so as to reduce delivering time. However, an item re-inspection passage portion 120 in other forms may be available.

In an embodiment, the security inspection passage further includes an item flow merging station 141, at which an item that has not been inspected is delivered to the inspection passage entrance end portion 112 and to which the item re-inspection passage portion 120 delivers a suspected item.

In an embodiment, a suspected item enters the inspection passage main portion 111 at the item flow merging station 141, is delivered to the item distribution station 142, then is transferred to the item re-inspection passage portion 120, and finally is delivered to the item flow merging station 141, completing an inspection cycle. In this way, the suspected item may enter the inspection passage main portion 111 for another inspection.

In an embodiment, in a situation where items to be inspected are small or scattered, such as wallet, mobile, phone, camera and the like, an item container may be used, such as a tray in which the item to be inspected may be collected for inspection. The tray where the items are contained is firstly delivered to the item flow merging station 141 and then to the inspection passage entrance end portion 112 from the item flow merging station 141, and passes through the inspection passage main portion 111, and enters the item flow diversion station 142 from the inspection passage exit end portion 113. At the item flow diversion station 142, the tray will be diverted to the suspected item passage portion 116 if the item carries a suspected article, and then is transferred to the item re-inspection passage portion 120 and is delivered to the item flow merging station 114 for inspection again. A beginning point of the item re-inspection passage portion is located near the suspected item passage portion such that the suspected item can be transferred to the item re-inspection passage portion.

In an embodiment, the tray is provided with a marker, such as a dimension code or a two-dimension code. When the item contained in the tray carries a suspected article, the inspection system or an additional device of the security inspection passage recognizes the marker and transmits information to the recognition system of the item flow diversion station 142. The recognition system of the item flow diversion station 142 recognizes the marker to recognize the tray that contains a suspected item, thereby allowing the tray to be diverted to the suspected item passage portion 116. In an embodiment, another tray that has no suspected item may be diverted from the item flow diversion station 142 to the secure item passage portion 115.

In an embodiment, the security inspection passage further includes an item container back-delivering passage portion configured to deliver an item container configured to contain an item to be inspected therein to near the inspection passage entrance end portion 112. At item flow diversion station 142, a secured item is diverted to the secured item passage portion 115 and is further delivered to an item container recovery station 131. The item container recovery station 131 is configured to recover the item container (which is configured to contain an item therein) from the secured item passage portion and transfer the item container to the item container back-delivering passage portion. When the item container is emptied, it is delivered to the item container back-delivering passage portion and is delivered to the beginning point for the inspection to be used again.

Figure 2:
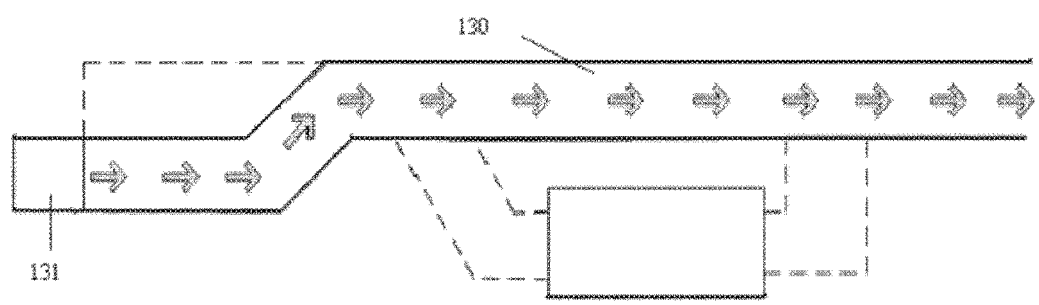
FIG. 2 illustrates a plan view of a lower level of a security inspection passage according to an embodiment, in which the dashed line denotes the upper level of the security inspection passage.
Figure 3:
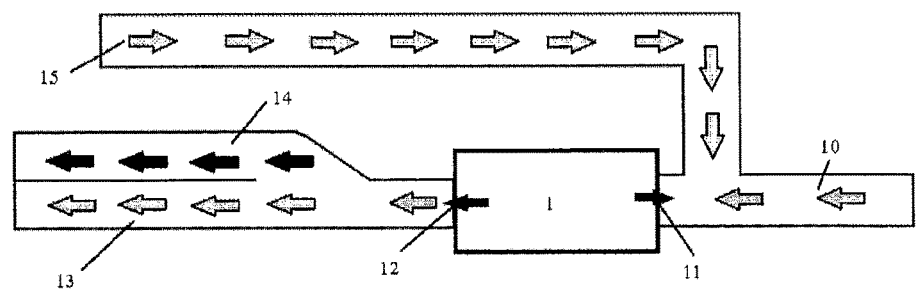
FIG. 3 illustrates a schematic view of a security passage.

In an embodiment, the inspection passage main portion 111 is located at an almost same level in height as the item re-inspection passage portion 120, for example, they are located at an upper level. Meanwhile, the item container back-delivering passage portion is desirably located below the item re-inspection passage portion 120, in other words, it is located at a lower level. In this way, the space below the item re-inspection passage portion 120 may be used fully. In the embodiment, as shown in FIG. 1, the suspected item passage portion 116 and the secure item passage portion 115 may be located at an upper level. Referring to FIGS. 1 and 2, the item container recovery station 131 is located at an end point of the secure item passage portion 115. At the item container recovery station 131, the item will be taken away and the item container may be transferred to the item container back-delivering passage portion. As shown in FIG. 2, an item container recovering passage 130 of the item container back-delivering passage portion is located at the lower level and extends from left to right in the plane of the page of FIG. 2 (as shown by the arrow in FIG. 2). The item container back-delivering passage portion may be located below the item re-inspection passage portion 120 and extends in the same direction.

In an embodiment, the inspection passage has the inspection passage entrance end portion 112 and the inspection passage exit end portion 113 which, for example, are arranged in a way to deviate from the direction in which the inspection passage main portion 111 extends, accordingly, the inspection passage has a curved form as a whole. The inspection passage entrance end and the inspection passage exit end may be located at a same straight line as the item re-inspection passage portion 120. As shown in FIG. 1, the inspection passage entrance end is located near the end point of the item re-inspection passage portion 120, i.e., near the item flow merging station 141, and the inspection passage exit end is located near the beginning point of the item re-inspection passage portion 120, i.e., near the item flow diversion station 142. The inspection passage main portion 111 extends in another straight line that is parallel to the item re-inspection passage portion 120 and is arranged substantially at the same level in height as the item re-inspection passage portion 120. The item flow diversion station 142 is located near the beginning point of the item re-inspection passage portion 120 and is configured to divert the items into two directions in the page of FIG. 1, i.e., to divert the item downwardly in the page of FIG. 1 to the secure item passage portion 115, or divert the item in the original direction to the suspected item passage portion 116. In this way, the secure item passage portion 115 and the suspected item passage portion 116 extend from the item flow diversion station 142 in two routes. In the embodiment, they extend from right to left in the page of FIG. 1 and are substantially parallel to each other.

Generally, the inspection passage main portion 111 is provided with a radiation source and a detector device of a large scale and thus the radiation source and the detector device occupy a significant amount of space at location where inspection passage main portion 111 is arranged. In other words, devices of the inspection passage main portion 111 are fixed on the ground and occupy a large space from up to down in a direction out and into to the page of FIG. 1. However, the item re-inspection passage portion 120 does not occupy such a great space and a lower space below the item re-inspection passage portion 120 is empty. According to the embodiment, the item container back-delivering passage portion is disposed below the item re-inspection passage portion 120 so that the space may be fully used and the entire apparatus may be compact.

In an embodiment, an item to be inspected enters the inspection passage main portion 111 from the flow merging station 141 and is diverted at the item flow diversion station 142. In some situations, the item will be delivered back to the flow merging station 141 via the item re-inspection passage portion 120. In some other situations, the item has been inspected to be secured and is delivered to the item container recovery station 131, waiting to be taken away. The item container is delivered back to near the item flow merging station 141 through the item container back-delivering passage portion.

According to an embodiment, the passages for inspecting and re-inspecting the item are arranged on the upper level while the passage for recycling the item container is arranged at the lower level such that the suspected item may be circulated and delivered through the inspection passage main portion 111 and the item re-inspection passage portion 120. The space below the item re-inspection passage portion 120 is used for arranging the item container recovering passage 130 such that the item container may be circulated and delivered through the inspection passage main portion 111 and the item container recovering passage 130.

In an embodiment, the security inspection passage further includes item introducing passage 110, through which an item to be inspected is delivered to the item flow merging station 141.

According to an embodiment, there is provided a security inspection apparatus, comprising a radiation source configured to emit radiation beams; a detection device configured to detect radiation beams transmitted through an item to be inspected; and the abovementioned security inspection passage.

In an embodiment, there is provided a security inspection apparatus, comprising a radiation source configured to emit radiation beams; a detection device configured to detect radiation beams transmitted through an item to be inspected; the abovementioned security inspection passage; and a central control device. The central control device may inspect the item that passes through the inspection passage main portion 111 and judge whether or not the item carries a suspected article. If a tray contains an item that carries a suspected article, the central control device recognizes a marker, such as an identification code on the tray, and transmits information to the recognition system of the item flow diversion station 142. When the tray is delivered to the item flow diversion station 142, the recognition system of the item flow diversion station 142 may recognize the tray and diverts the tray to the suspected item passage portion 116 so as to deliver it to the item re-inspection passage portion 120.

Although several exemplary embodiments of the present invention have been shown and described, it would be appreciated by those skilled in the art that various changes or modifications may be made in these embodiments without departing from the principles and spirit of the present invention, the scope of which is defined in the claims and their equivalents.

What is claimed is:

1. A security inspection passage system comprising:
   an inspection passage main portion structure that extends along a first direction and through which an item to be inspected passes so as to receive an inspection;

an inspection passage entrance end portion configured to be oriented in a direction that is angled at a first angle relative to the first direction;

an inspection passage exit end portion configured to be oriented in a direction that is angled at a second angle relative to the first direction, wherein the first angle and/or the second angle are/is not zero and wherein the inspection passage entrance end portion and the inspection passage exit end portion each have at least a part thereof located at, or facing toward, a same side of the inspection passage main portion;

an item flow diversion station, a secured item passage portion and a suspected item passage portion, wherein the inspection passage exit end portion is communicatively connected with the item flow diversion station such that items which have been inspected are divided into two parts, one part are items that are secured or non-suspected and are diverted to the secured item passage portion, and the other part are items that are suspected or which need to be re-inspected and are diverted to the suspected item passage portion;

an item re-inspection passage portion configured to deliver items to be re-inspected back to the inspection passage entrance end portion, wherein a beginning point of the item re-inspection passage portion is located at the suspected item passage portion to allow items from the suspected item passage portion to be transferred to the item re-inspection passage portion and wherein the item re-inspection passage portion extends in a second direction that is opposite to the first direction and delivers items in a direction opposite to the direction in which the inspection passage main portion delivers items; and an item flow merging station, at which an item that has not been inspected is delivered to the inspection passage entrance end portion and to which the item re-inspection passage portion delivers an item.

2. The security inspection passage system of claim 1, wherein the inspection passage main portion structure comprises a radiation shielding device configured to prevent radiation within the inspection passage main portion structure from propagating out of the inspection passage main portion structure, the radiation shielding device arranged in the inspection passage entrance end portion and the inspection passage exit end portion to prevent leakage of the radiation.

3. The security inspection passage system of claim 1, further comprising an item container recovery station configured to recover an item container from the secured item passage portion and transfer the item container to an item container back-delivering passage portion.

4. The security inspection passage system of claim 3, configured to allow the secured or non-suspected items to be delivered, via the secured item passage portion, to the item container recovery station, and to allow the secured or non-suspected items to be recovered when being on the secured item passage portion.

5. The security inspection passage system of claim 1, wherein the inspection passage main portion structure extends along a straight line.

6. A security inspection apparatus comprising: a radiation source configured to emit a radiation beam, a detection device configured to detect the radiation beam transmitted through an item to be inspected, and the security inspection passage system of claim 1.

7. The security inspection passage system of claim 1, wherein at least part of the inspection passage main portion structure and at least part of the item re-inspection passage portion are side-by-side at a same height.

8. The security inspection passage system of claim 1, wherein the suspected item passage portion and the item re-inspection passage portion extend along an essentially straight line.

9. The security inspection passage system of claim 1, wherein the item flow diversion station, the item re-inspection passage portion, and the item flow merging station are arranged along an essentially straight line.

10. The security inspection passage system of claim 1, further comprising an item container back-delivering passage portion configured to deliver an item container configured to contain an item to be inspected therein, to be located at the inspection passage entrance end portion, wherein the item container back-delivering passage portion is located below the item re-inspection passage portion.

11. A security inspection method, comprising:
passing items to be inspected through an inspection passage main portion that extends along a first direction so as to receive an inspection;

passing items through an inspection passage entrance end portion oriented in a direction that is angled at a first angle relative to the first direction;

passing items through an inspection passage exit end portion oriented in a direction that is angled at a second angle relative to the first direction, wherein the first angle and/or the second angle are/is not zero and wherein the inspection passage entrance end portion and the inspection passage exit end portion each have at least a part thereof located at, or facing toward, a same side of the inspection passage main portion;

passing items through an item flow diversion station, a secured item passage portion and a suspected item passage portion, wherein the inspection passage exit end portion is communicatively connected with the item flow diversion station such that items which have been inspected are divided into two parts, one part are items that are secured or non-suspected and are diverted to the secured item passage portion, and the other part are items that are suspected or which need to be re-inspected and are diverted to the suspected item passage portion;

delivering items to be re-inspected back to the inspection passage entrance end portion using an item re-inspection passage portion, wherein a beginning point of the item re-inspection passage portion is located at the suspected item passage portion to allow items from the suspected item passage portion to be transferred to the item re-inspection passage portion and the item re-inspection passage portion extends in a second direction that is opposite to the first direction and delivers items therein in a direction opposite to the direction in which the inspection passage main portion delivers items; and using an item flow merging station to deliver an item that has not been inspected to the inspection passage entrance end portion, wherein the item re-inspection passage portion delivers an item to the item flow merging station.

12. The method of claim 11, further comprising preventing radiation within the inspection passage main portion from propagating out of the inspection passage main portion using a radiation shielding device, the radiation shielding device arranged in the inspection passage entrance end portion and the inspection passage exit end portion to prevent leakage of the radiation.

13. The method of claim 11, further comprising using an item container recovery station to recover an item container from the secured item passage portion and to transfer the item container to an item container back-delivering passage portion.

14. The method of claim 13, comprising delivering the secured or non-suspected items, via the secured item passage portion, to the item container recovery station, wherein the secured item passage portion is arranged to allow the secured or non-suspected item to be recovered when being on the secured item passage portion.

15. The method of claim 11, wherein the inspection passage main portion extends along a straight line.

16. The method of claim 11, wherein at least part of the inspection passage main portion and at least part of the item re-inspection passage portion are side-by-side at a same height.

17. The method of claim 11, wherein the suspected item passage portion and the item re-inspection passage portion extend along an essentially straight line.

18. The method of claim 11, further comprising delivering an item container configured to contain an item to be inspected therein, to be located at the inspection passage entrance end portion using an item container back-delivering passage portion, wherein the item container back-delivering passage portion is located underneath the item re-inspection passage portion.

19. A security inspection passage system comprising:
an inspection passage main portion structure that is elongate along a first direction and through which an item to be inspected travels in the first direction so as to receive an inspection;
an inspection passage entrance end portion configured to be oriented in a direction that is angled at a first angle relative to the first direction;
an inspection passage exit end portion configured to be oriented in a direction that is angled at a second angle relative to the first direction, wherein the first angle and/or the second angle are/is not zero;
an item flow diversion station, a secured item passage portion and a suspected item passage portion, wherein the inspection passage exit end portion is communicatively connected with the item flow diversion station such that items which have been inspected are divided into two parts, one part are items that are secured or non-suspected and are diverted to the secured item passage portion, and the other part are items that are suspected or which need to be re-inspected and are diverted to the suspected item passage portion;
an item re-inspection passage portion configured to deliver items to be re-inspected back to the inspection passage entrance end portion, wherein a beginning point of the item re-inspection passage portion is located at the suspected item passage portion to allow items from the suspected item passage portion to be transferred to the item re-inspection passage portion; and
an item flow merging station, at which an item is delivered to the inspection passage entrance end portion and to which the item re-inspection passage portion delivers an item,
wherein the suspected item passage portion, the item re-inspection passage portion and item flow merging station are all on a same side of the inspection passage main portion structure, the same side extending along the first direction.

20. The security inspection passage system of claim 19, wherein the item flow diversion station, the item re-inspection passage portion, and the item flow merging station are arranged along an essentially straight line.

* * * * *